US00PP29473P3

(12) United States Plant Patent
Hines, III

(10) Patent No.: US PP29,473 P3
(45) Date of Patent: Jul. 10, 2018

(54) ***NYSSA* PLANT NAMED 'THE JAMES'**

(50) Latin Name: *Nyssa sylvatica*
Varietal Denomination: The James

(71) Applicant: James A. Hines, III, McMinnville, TN (US)

(72) Inventor: James A. Hines, III, McMinnville, TN (US)

( * ) Notice: Subject to any disclaimer, the term of this patent is extended or adjusted under 35 U.S.C. 154(b) by 49 days.

(21) Appl. No.: 15/530,038

(22) Filed: Nov. 22, 2016

(65) Prior Publication Data

US 2018/0146585 P1 May 24, 2018

(51) Int. Cl.
*A01H 5/12* (2018.01)
*A01H 5/04* (2018.01)

(52) U.S. Cl.
USPC ..... Plt./216
CPC ..... *A01H 5/04* (2013.01); *A01H 5/12* (2013.01)

(58) Field of Classification Search
USPC ..... Plt./216
See application file for complete search history.

*Primary Examiner* — Anne Marie Grunberg
(74) *Attorney, Agent, or Firm* — C. A. Whealy

(57) ABSTRACT

A new and distinct cultivar of *Nyssa* tree named 'The James', characterized by its broadly ovate tree form with upswept branching habit; vigorous growth habit; freely branching habit with numerous lateral branches providing a full and densely foliated appearance; large glossy dark green-colored leaves that become orangish red in color during the autumn; and red-colored leaf petioles.

4 Drawing Sheets

Botanical designation: *Nyssa sylvatica.*
Cultivar denomination: 'THE JAMES'.

BACKGROUND OF THE INVENTION

The present invention relates to a new and distinct cultivar of *Nyssa* tree, botanically known as *Nyssa sylvatica*, commercially referred to as Upland Tupelo or Black Gum and hereinafter referred to by the name 'The James'.

The new *Nyssa* tree is a naturally-occurring branch mutation of *Nyssa sylvatica* 'Wildfire', not patented. The new *Nyssa* tree was discovered and selected by the Inventor on a single tree in a outdoor nursery environment in McMinnville, Tenn. on Aug. 31, 2013.

Asexual reproduction of the new *Nyssa* tree by chip budding in a controlled environment in McMinnville, Tenn. since March, 2014, has shown that the unique features of this new *Nyssa* tree are stable and reproduced true to type in successive generations.

SUMMARY OF THE INVENTION

Trees of the new *Nyssa* have not been observed under all possible combinations of environmental and cultural conditions. The phenotype may vary somewhat with variations in environmental conditions such as temperature and light intensity without, however, any variance in genotype.

The following traits have been repeatedly observed and are determined to be the unique characteristics of 'The James'. These characteristics in combination distinguish 'The James' as a new and distinct *Nyssa* tree:

1. Broadly ovate tree form with upswept branching habit.
2. Vigorous growth habit.
3. Freely branching habit with numerous lateral branches providing a full and densely foliated appearance.

4. Large glossy dark green-colored leaves that become orangish red in color during the autumn.
5. Red-colored leaf petioles.

Trees of the new *Nyssa* can be compared to trees of the mutation parent, 'Wildfire'. Trees of the new *Nyssa* differ primarily from trees of 'Wildfire' in the following characteristics:

1. Trees of the new *Nyssa* are more vigorous than trees of 'Wildfire'.
2. Trees of the new *Nyssa* have dark green-colored leaves whereas plants of 'Wildfire' have dark green-colored leaves with red-colored apices.

Trees of the new *Nyssa* can be compared to trees of *Nyssa sylvatica* 'Tupelo Power', not patented. Trees of the new *Nyssa* and 'Tupelo Power' differ primarily in the following characteristics:

1. Trees of the new *Nyssa* have broader branch angles and are broader in overall plant form than trees of 'Tupelo Power'.
2. Trees of the new *Nyssa* are more vigorous than trees of 'Tupelo Power'.
3. Trees of the new *Nyssa* are more densely foliated than trees of 'Tupelo Power'.
4. Leaves of trees of the new *Nyssa* have red-colored petioles whereas leaves of trees of 'Tupelo Power' have green-colored petioles.

Trees of the new *Nyssa* can also be compared to trees of *Nyssa sylvatica* 'Forum', not patented. Trees of the new *Nyssa* and 'Forum' differ primarily in the following characteristics:

1. Trees of the new *Nyssa* are more densely foliated than trees of 'Forum'.
2. Trees of the new *Nyssa* have broader and glossier leaves than trees of 'Forum'.

3. Leaves of trees of the new *Nyssa* are orangish red in color during the autumn whereas leaves of trees of 'Forum' are dark red in color during the autumn.
4. Leaves of trees of the new *Nyssa* have red-colored petioles whereas leaves of trees of 'Forum' have green-colored petioles.

BRIEF DESCRIPTION OF THE PHOTOGRAPHS

The accompanying colored photographs illustrate the overall appearance of the new *Nyssa* tree showing the colors as true as it is reasonably possible to obtain in colored reproductions of this type. Colors in the photographs may differ slightly from the color values cited in the detailed botanical description which accurately describe the colors of the new *Nyssa* tree.

The photograph on the first sheet is a side perspective view of typical trees of 'The James' grown during the summer in an outdoor nursery.

The photograph on the second sheet is a close-up view of a typical tree of 'The James' grown during the summer.

The photograph on the third sheet is a side perspective view of typical trees of 'The James' grown during the autumn in an outdoor nursery.

The photograph on the fourth sheet is a close-up view of a typical tree of 'The James' grown during the autumn.

DETAILED BOTANICAL DESCRIPTION

The aforementioned photographs and following observations, measurements and values describe trees grown in 15-gallon containers in an outdoor nursery in McMinnville, Tenn. and under cultural practices typical of commercial *Nyssa* tree production. Trees used in the photographs and description were four years old. During the production of the trees, day temperatures averaged 20.9° C. and night temperatures averaged 8.4° C. In the following description, color references are made to The Royal Horticultural Society Colour Chart, 2007 Edition, except where general terms of ordinary dictionary significance are used.

Botanical classification: *Nyssa sylvatica* 'The James'.

Parentage: Naturally-occurring branch mutation of *Nyssa sylvatica* 'Wildfire', not patented.

Propagation:

*Type*.—By chip budding the new *Nyssa* tree onto an unnamed selection of *Nyssa sylvatica* understock.

Tree description:

*Tree form and growth habit*.—Deciduous tree with broadly ovate form with upswept branching habit; vigorous growth habit; freely branching habit with numerous lateral branches providing a full and densely foliated appearance; about 35 primary lateral branches per tree and secondary branches potentially developing at every node.

*Tree height*.—About 2.6 meters.

*Tree width* (*spread*).—About 95 cm.

*Trunk caliper*.—About 4 cm.

*Branch angle orientation*.—Mid-tree canopy branches, about 50° from vertical.

*Internode length*.—About 3.2 cm on one-year old wood.

*Lateral branch texture*.—Smooth, glabrous.

*Mature bark texture*.—Woody; smooth, glabrous.

*Lateral branch color*.—Close to 144A, with development, tinged with close to 165A, and with subsequent development, becoming closer to 200C.

*Mature bark color*.—Darker brown than N200B.

Leaf description:

*Arrangement*.—Alternate, simple.

*Length*.—About 10.4 cm.

*Width*.—About 4.4 cm.

*Shape*.—Obovate.

*Apex*.—Acuminate with cuspidate tendencies.

*Base*.—Cuneate.

*Margins*.—Entire.

*Venation pattern*.—Pinnate.

*Texture, upper and lower surfaces*.—Smooth, glabrous.

*Luster, upper surface*.—Glossy.

*Luster, lower surface*.—Matte.

*Color*.—When developing, upper surface: More green than 147A. When developing, lower surface: Close to N137A. Fully developed, upper surface: Darker and more green than 147A; in the autumn, variable sectors, close to 44A, 45A and 46A; venation, close to 146A. Fully developed, lower surface: Close to 146A; in the autumn, variable sectors, close to 50C to 50D and 51C to 51D; venation, close to 145C.

*Petioles*.—Length: About 1.7 cm. Diameter: About 2.5 mm. Texture, upper and lower surfaces: Smooth, glabrous. Color, upper surface: Close to 145A overlain with close to 46A. Color, lower surface: Close to 145B overlain with close to 46A.

Flower description: Flower initiation and development have not been observed on trees of the new *Nyssa* to date.

Temperature tolerance: Trees of the new *Nyssa* have been observed to tolerate high temperatures about 43° C. and low temperatures about −29° C. when grown in USDA Hardiness Zone 6.

Pathogen & pest resistance: Trees of the new *Nyssa* have been observed to be resistant to Leaf Spot (*Mycosphaerella nyssicola*). Trees of the new *Nyssa* have not been observed to be resistant to pests and other pathogens common to *Nyssa* trees.

It is claimed:

1. A new and distinct *Nyssa* tree named 'The James' as illustrated and described.

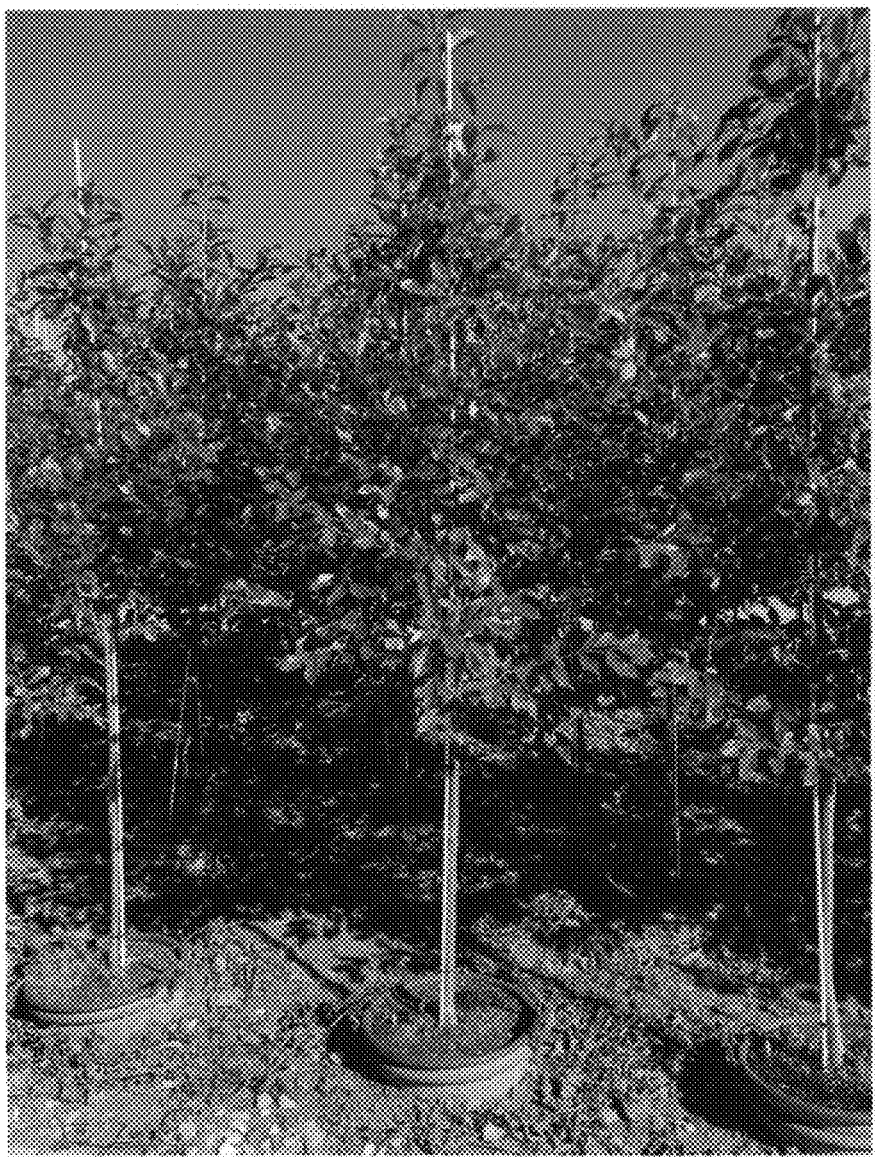

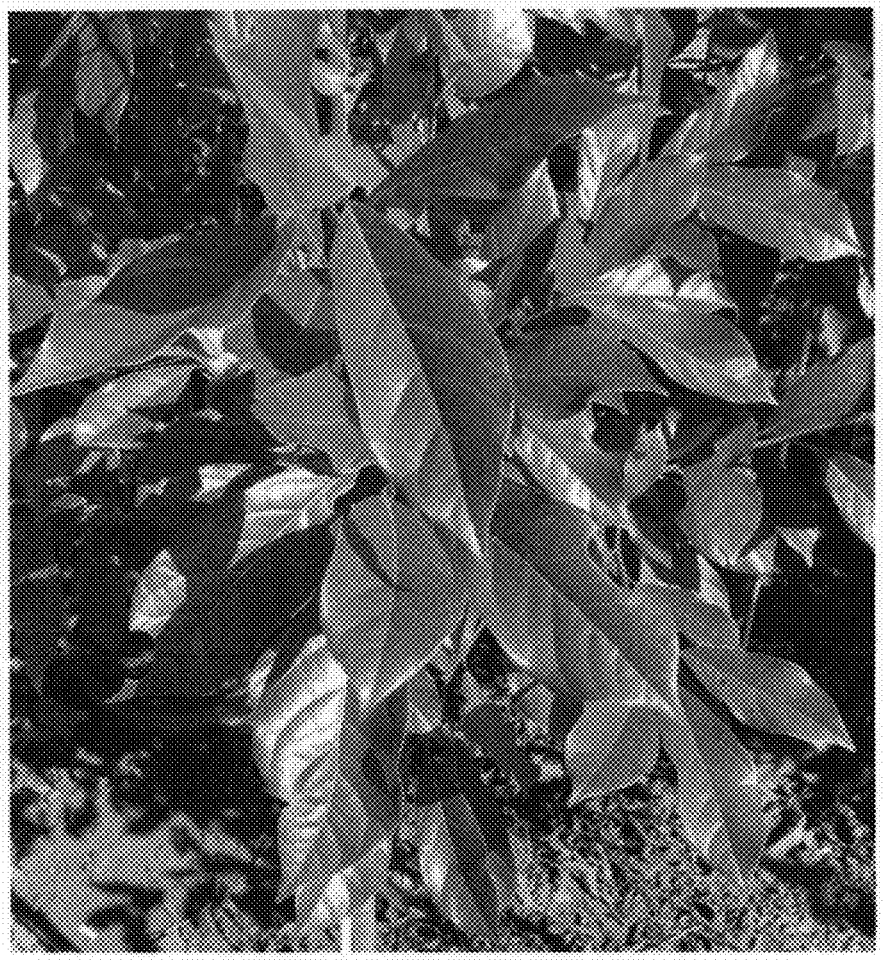

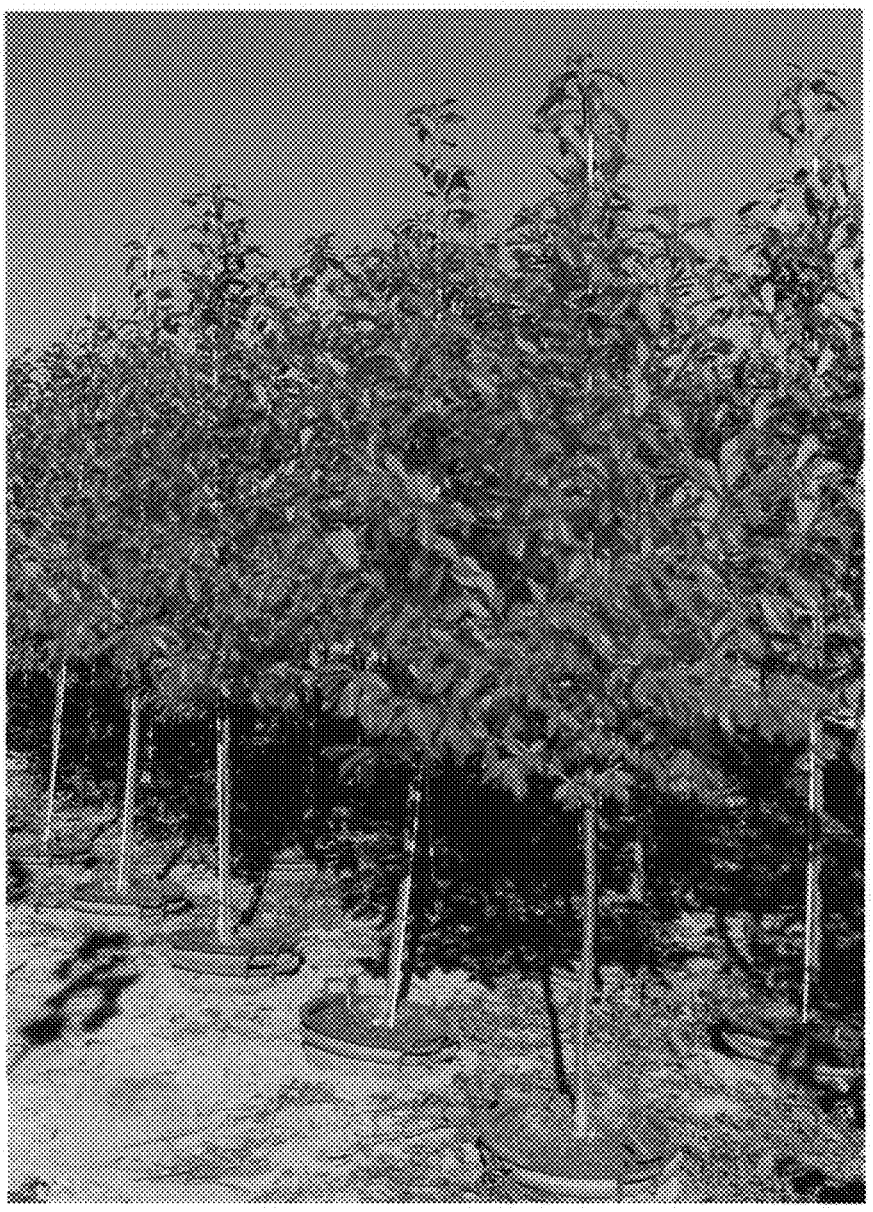

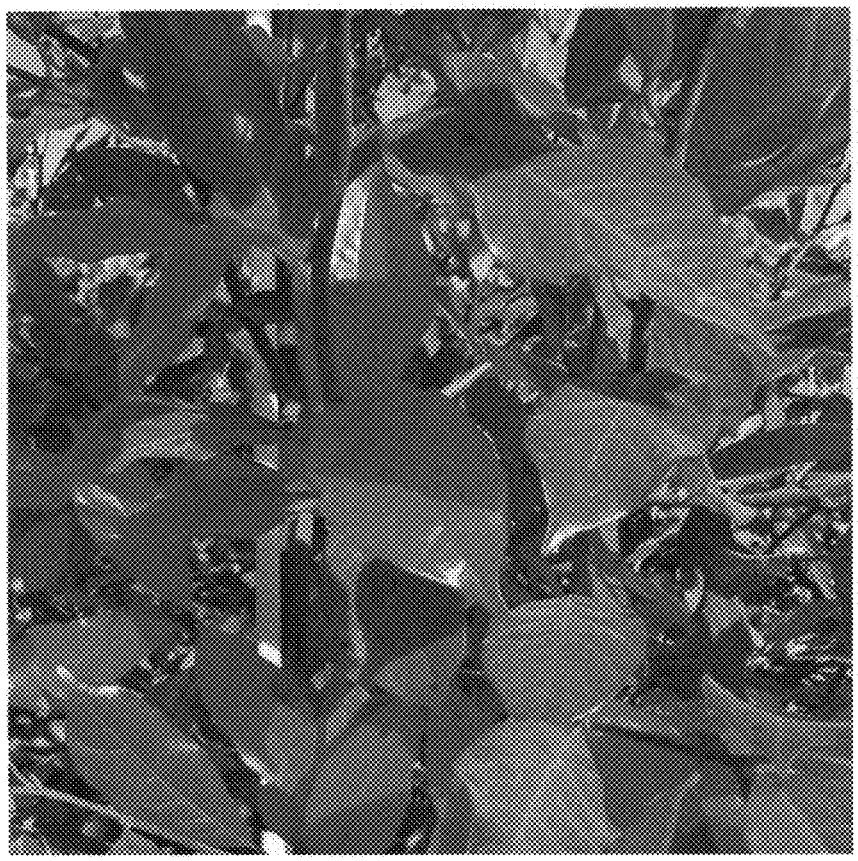

* * * * *